United States Patent
Mikus et al.

(10) Patent No.: US 6,694,170 B1
(45) Date of Patent: Feb. 17, 2004

(54) COMPUTER GUIDED SURGERY FOR PROSTATIC NERVE SPARING

(75) Inventors: Paul W. Mikus, Irvine, CA (US); Jay Eum, Irvine, CA (US); John C. Rewcastle, Dana Point, CA (US); Jawahar M. Ali, Mission Viejo, CA (US)

(73) Assignee: Endocare, Inc., Irvine, CA (US)

( * ) Notice: Subject to any disclaimer, the term of this patent is extended or adjusted under 35 U.S.C. 154(b) by 71 days.

(21) Appl. No.: 09/981,336

(22) Filed: Oct. 16, 2001

Related U.S. Application Data (63) Continuation-in-part of application No. 09/699,938, filed on Oct. 30, 2000, now Pat. No. 6,485,422, which is a continuation of application No. 09/318,710, filed on May 26, 1999, now Pat. No. 6,139,544.

(51) Int. Cl.[7] ................................................. A61B 5/05
(52) U.S. Cl. ...................... 600/427; 600/407; 128/920; 606/21
(58) Field of Search ................................ 600/407, 411, 600/427, 439, 3, 12; 606/21, 22; 128/920

(56) References Cited

U.S. PATENT DOCUMENTS

| | | | | |
|---|---|---|---|---|
| 4,672,963 A | | 6/1987 | Barken | 128/303.1 |
| 5,366,490 A | * | 11/1994 | Edwards et al. | 607/99 |
| 5,531,742 A | | 7/1996 | Barken | 606/21 |
| 5,647,868 A | * | 7/1997 | Chinn | 606/21 |
| 5,706,810 A | | 1/1998 | Rubinsky | 128/653.1 |
| 5,800,488 A | * | 9/1998 | Crockett | 607/105 |
| 5,810,007 A | * | 9/1998 | Holupka et al. | 600/439 |
| 5,882,306 A | | 3/1999 | Ramamurthy | 600/440 |
| 6,041,787 A | * | 3/2000 | Rubinsky | 128/898 |
| 6,083,166 A | | 7/2000 | Holdaway | 600/439 |
| 6,095,975 A | * | 8/2000 | Silvern | 600/439 |
| 6,139,544 A | | 10/2000 | Mikus | 606/21 |
| 6,142,991 A | * | 11/2000 | Schatzberger | 606/21 |
| 6,256,529 B1 | * | 7/2001 | Holupka et al. | 600/427 |

OTHER PUBLICATIONS

Littrup et al., Prostate Cryosurgery Complications.
Onik, Ultrasound–Guided Cryosurgery, Scientific American at 62 (Jan. 1996).
Onik, Cohen, et al. Transrectal Ultrasound–Guided Percutaneous Radical Cryosurgical Ablation of the Prostate, 72 Cancer 1291 (1993).

* cited by examiner

*Primary Examiner*—Dennis W. Ruhl
*Assistant Examiner*—Runa Shah Qaderi
(74) *Attorney, Agent, or Firm*—Lawrence N. Ginsberg (57) ABSTRACT

The computer system is capable of acquiring and displaying images of the prostate of a patient for assisting a surgeon in placing ablative elements in the prostate of the patient. The computer system is programmed with software capable of: 1) determining the dimensions of the prostate; and, 2) determining the dimensions and location of a treatment zone. The treatment zone is determined to include only one neurovascular bundle of the prostate and exclude the other neurovascular bundle of the prostate. The system utilizes the determined dimensions of the prostate and treatment zone for computing the number and location of ablative elements needed to treat the treatment zone while minimizing any adverse effect on the patient's sexual function.

15 Claims, 6 Drawing Sheets

COMPUTER GUIDED SURGERY FOR PROSTATIC NERVE SPARING

CROSS REFERENCE TO RELATED APPLICATIONS

This application is a continuation-in-part of U.S. Ser. No. 09/699,938 now U.S. Pat. No. 6,485,422, filed Oct. 30, 2000, which is a continuation of U.S. Pat. No. 6,139,544, issued Oct. 31, 2000. (U.S. Ser. No. 09/318,710, filed May 26, 1999.)

BACKGROUND OF THE INVENTION

The present invention relates to prostatic surgery and more particularly to a computer guided system for focal, nerve sparing ablative surgery.

Ablative surgery of the prostate is an effective treatment for prostate cancer. There has been a focus in prostate cancer treatment development in trying to improve the quality of life of patients by limiting the effect of treatment on patient sexual functioning. For example, Littrup et al, in *Prostate Cryosurgery Complications*, Seminars In Interventional Radiology, Vol. II, No. 3, September 1994 discuss a protocol for potential nerve-sparing prostate cryosurgery for patients with evidence of unilateral disease. Littrup et al propose altering the placement of cryoprobes and close monitoring of the iceballs formed therefrom for patients with evidence of unilateral disease on standard systematic biopsies, followed by negative subcapsular biopsies. The cryoprobes are shifted toward the ipsilateral tumor side, leaving the potentially spared contralateral tissue.

There is reference in the prior art to the use of computer control systems for providing and/or enhancing cryosurgical techniques. For example, U.S. Pat. No. 4,672,963, issued to I. Barken, discloses an automated and integrated system including a cryosurgery device, an imaging probe and a computer system for use in performing internal surgery. U.S. Pat. No. 5,647,868, issued to D. O. Chinn, discloses another cryosurgical integrated control and monitoring system.

U.S. Pat. No. 6,139,544, issued to P. W. Mikus et al, discloses a system for assisting surgeons in performing cryosurgery of the prostate by calculating optimal positions for cryoprobes and providing display based templates for overlay over an ultrasound image display, and displaying actual cryoprobe ultrasound images together with template images so that the surgeon may compare suggested and actual placement of the cryoprobes, and adjust placement accordingly.

SUMMARY OF THE INVENTION

In one broad aspect, the present invention is a computer system for the focal treatment of prostate cancer. The computer system is capable of acquiring and displaying images of the prostate of a patient for assisting a surgeon in placing ablative elements in the prostate of the patient. The computer system is programmed with software capable of determining the dimensions of the prostate, determining the dimensions and location of a treatment zone; and, utilizing the determined dimensions of the prostate and treatment zone for computing the number and location of ablative elements needed to treat the treatment zone while minimizing any adverse effect on the patient's sexual function.

The step of utilizing the determined dimensions of the prostate and treatment zone, preferably comprises the steps of:

computing the number of ablative elements;

computing a distance (b) between the ablative elements so that the ablative elements are placed approximately equidistant from each other in the treatment zone;

computing a first position for placement of a first ablative element;

computing a second position for placement of a second ablative element, the second position being at the distance, b, from the first position and a distance a from the prostate periphery, wherein a is approximately ½ b; and, computing N-2 remaining positions for the ablative elements in substantially the same manner as the second position was computed.

The computer system is particularly adaptable for use in instances where a biopsy has indicated that unilateral ablative nerve sparing is warranted. In such instance one side of the prostate, including its associated neurovascular bundle is spared while the other is sacrificed. This can maintain potency for the patient.

Although particularly adaptable for use with cryoprobes, the inventive concepts disclosed herein can be utilized with other suitable ablative elements, as discussed below, that can provide the desired ablation.

DETAILED DESCRIPTION OF THE INVENTION

Figure 1:
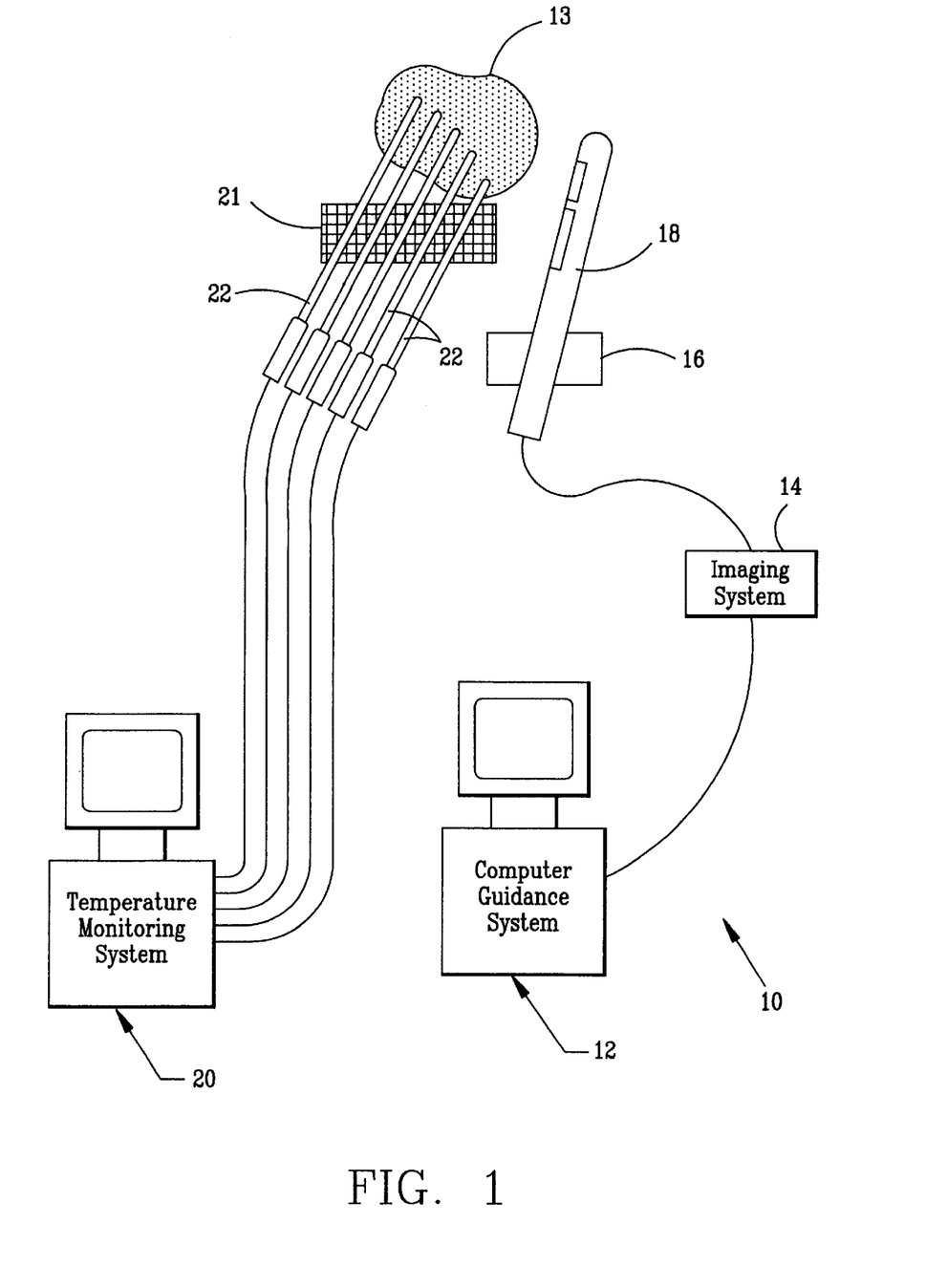
FIG. 1 is an overall system schematic of the present invention.

Referring now to the drawings and the characters of reference marked thereon, FIG. 1 illustrates a preferred embodiment of the prostatic nerve sparing system of the present invention, designated generally as 10. The system 10 includes a computer system 12 that provides guidance as to recommended ablative element placement within a prostate 13, based on images of the prostate acquired from an imaging system, such as an ultrasound system 14, 16, 18. An ablative treatment system 20, 22 provides the required prostatic ablation for nerve sparing. In this preferred embodiment the ablative treatment system includes a temperature monitoring system 20 connected to a plurality of ablative elements, e.g. cryoprobes 22.

The computer system 12 is programmed with software capable of: determining the dimensions of the prostate; determining the dimensions of a treatment zone; and, utilizing the determined dimensions of the prostate and treatment zone for computing the number and location of ablative elements needed to treat the treatment zone without adversely affecting the patient's sexual function.

Figure 2:
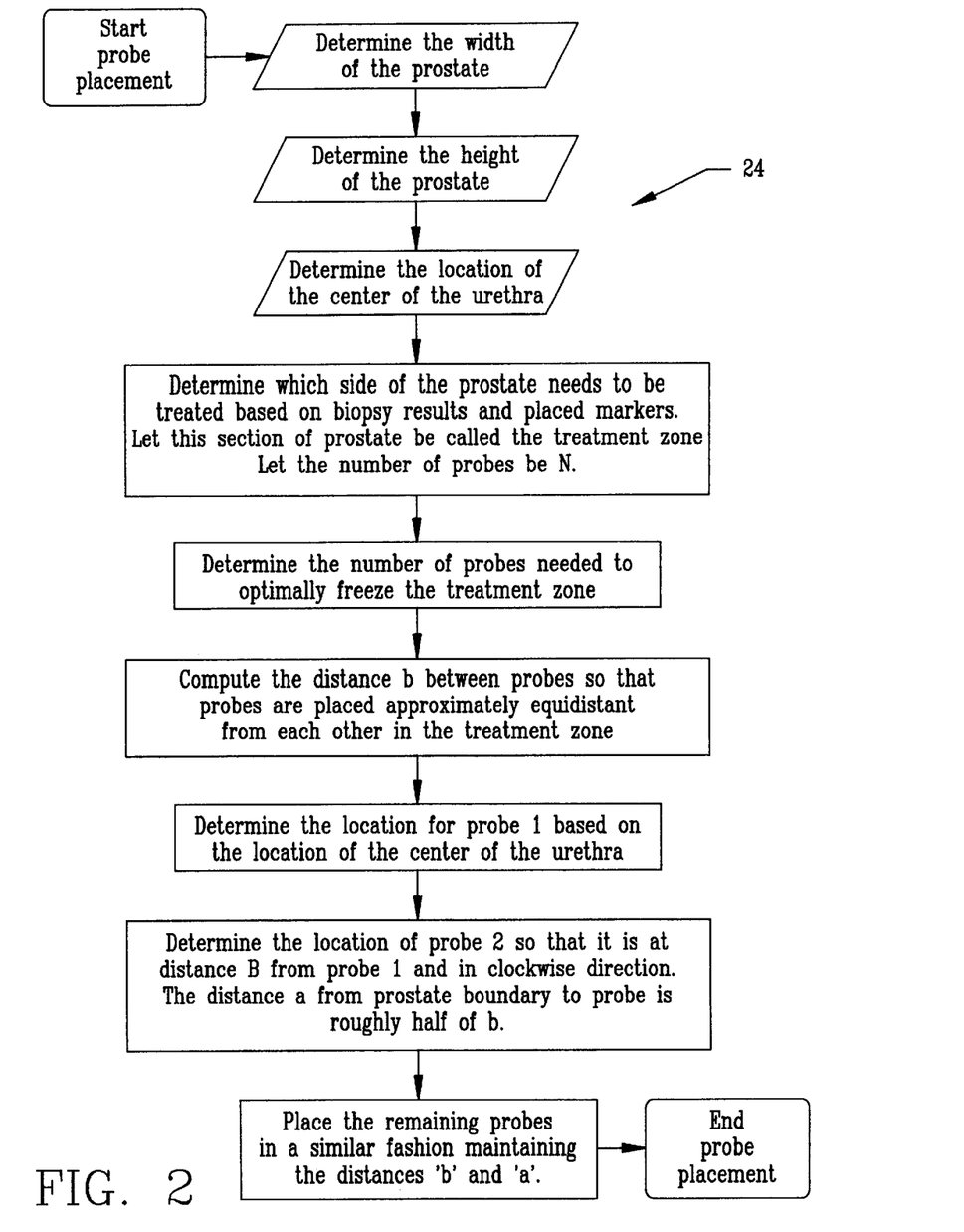
FIG. 2 is a flow chart of the preferred steps implemented by the computer system of the present invention.

Referring now to FIG. 2, a preferred embodiment of the steps required are illustrated, designated generally as 24. A plurality of images of the prostate are acquired using the imaging system. The imaging system may be an ultrasound, MRI, CT, PET, SPECT, X-ray (including fluoroscope) or other suitable imaging device. Additionally, the guidance system 12 determines the location of other anatomical structures of interest such as the urethra, neurovascular bundle and the rectal wall based on the acquired images. The system computes the width and height of the prostate and location of the urethra and neurovascular bundles. If the biopsy indicates that unilateral nerve sparing is warranted than graphical markers can be used to identify the side of the prostate that needs to be treated. These markers help in maintaining a consistent reference frame. In addition, the guidance system 12 also provides the user with an interface to specify the treatment zone. Once the treatment zone is identified the system 12 determines the dimensions of the treatment zone.

The number of cryoprobes can then be determined based on the above-computed dimensions. The location of the cryoprobes is determined by first computing a distance (b) between the cryoprobes so that the cryoprobes are placed approximately equidistant from each other in the treatment zone. A first position for placement of a cryoprobe is then determined based on the location of the urethra. A second position for placement of a cryoprobe is then determined. The second position is at the distance, b, from the first position and a distance a from the prostate periphery, wherein a is approximately ½ b. The N-2 remaining positions for the cryoprobes are computed in substantially the same manner as the second position was computed.

Figure 3:
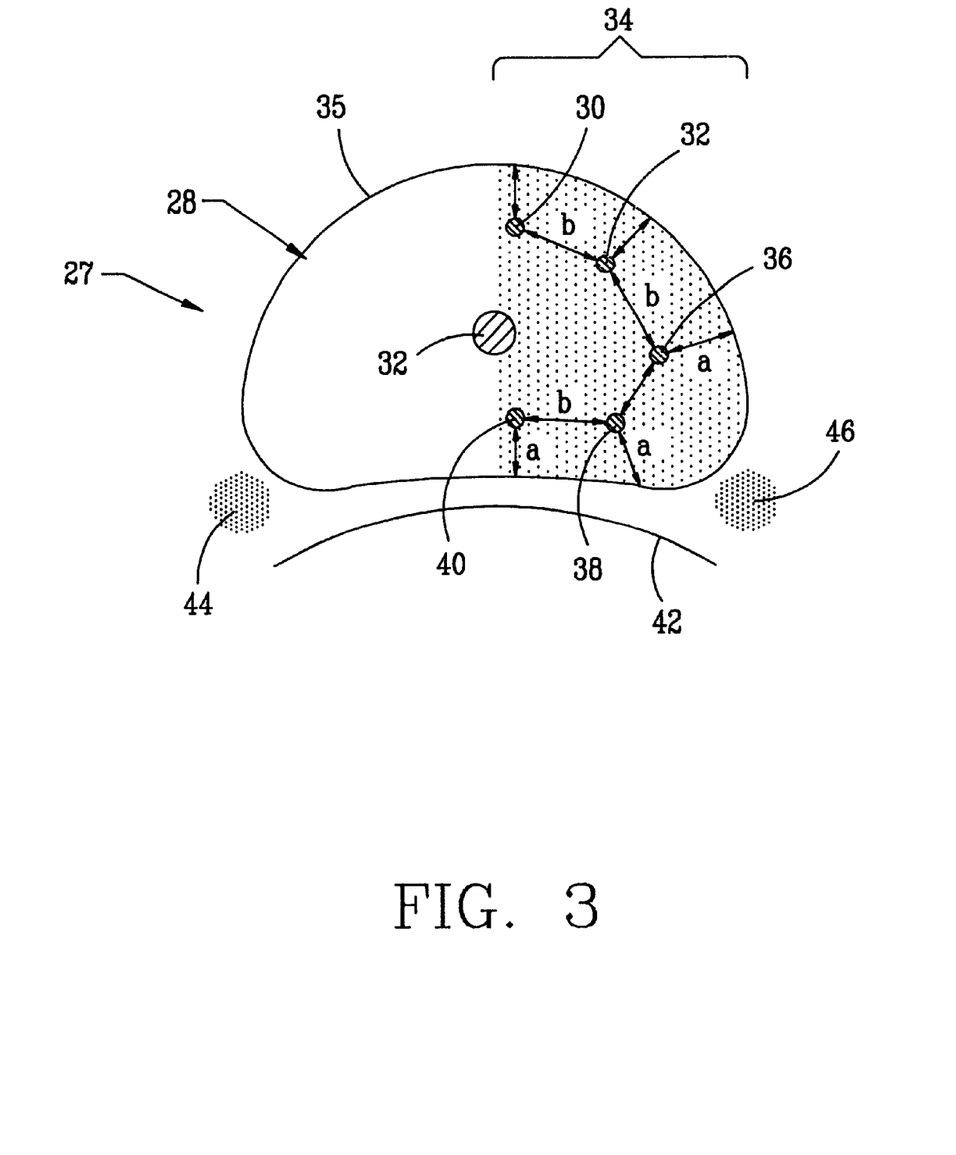
FIG. 3 is a transverse view of the prostate illustrating desired cryoprobe placements in accordance with the principles of the present invention.

Referring now to FIG. 3, a transverse view 27 of a prostate 28 is shown, illustrating such desired cryoprobe placement. The side of the prostate to be treated, i.e. treatment zone, is designated by reference bracket 34. A first position 30 for a first cryoprobe is shown which has been determined based on the location of the urethra 32. A second position 33 for a second cryoprobe is then determined by determining a location clockwise about the urethra 32 at a distance approximately a, from the periphery 35 of the prostate 28 and a distance, b, from the first position 30. Continuing in this clockwise direction about the prostate a third position 36 is determined. Similarly, fourth and fifth positions 38,40 are also determined. While determining the locations of the first and fifth positions, the positions are placed slightly off from the location of the center of the urethra so that the urethra is at a safe distance from these cryoprobe positions in all locations.

Although this procedure has been described with reference to positions being determined by clockwise determinations the procedure can alternatively be provided in the counterclockwise direction. (As discussed above, a reference point for determining cryoprobe placement can be the rectal wall.) The ultimate goal is to preserve the neurovascular bundle 44 on the side of the prostate 28 opposite the treatment zone 34. The other neurovascular bundle 46 can be sacrificed.

Figure 4:
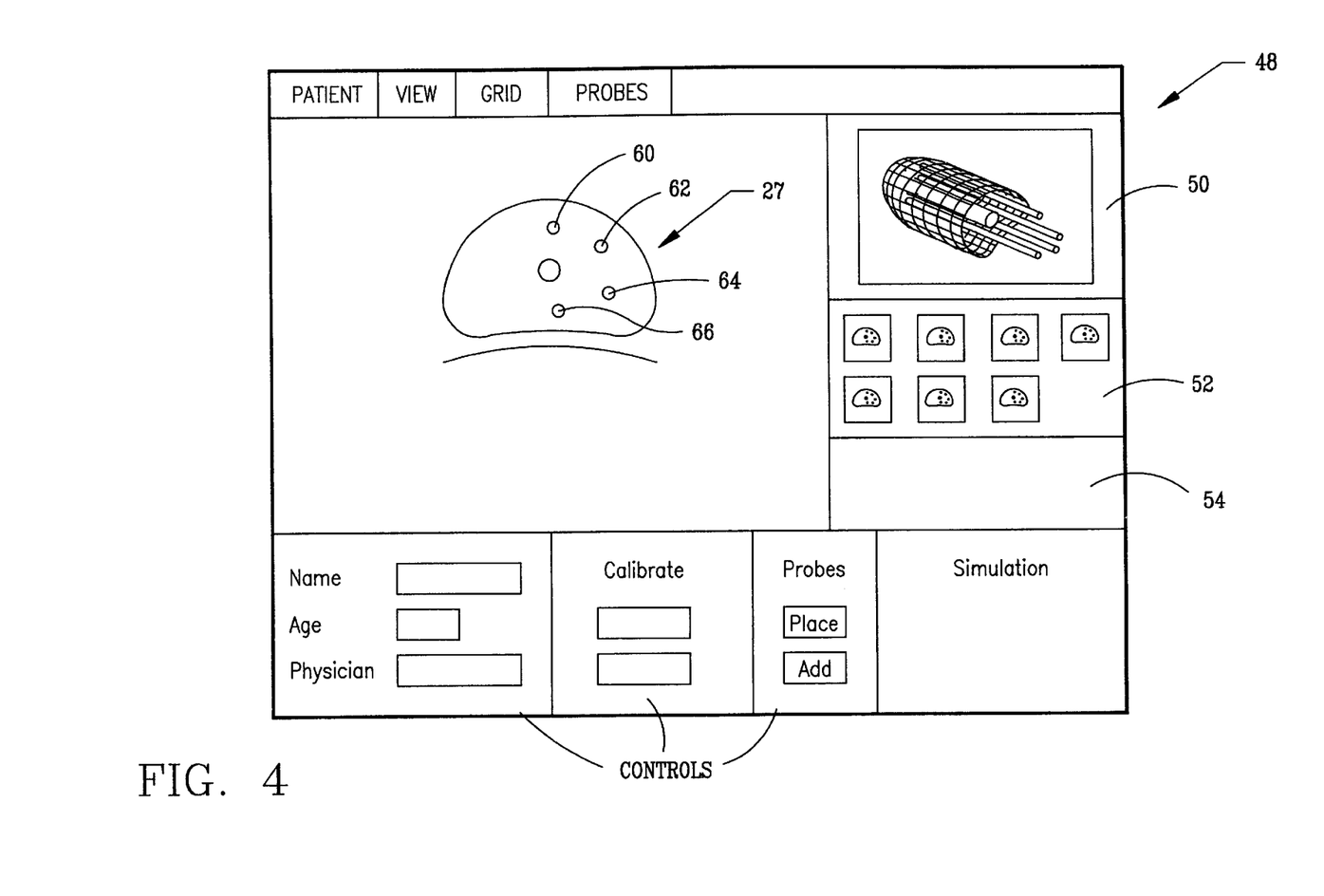
FIG. 4 is an example computer display from the computer guidance system of the present invention.

Referring now to FIG. 4 a sample display screen 48 of the computer system 12 showing the transverse view 27 is illustrated. A series of transverse images of the prostate which are acquired from the imaging system are utilized to reconstruct a three-dimensional model 50 of the prostate and other anatomical structures. The 3-D models help the physician visualize the organs and understand the location of the treatment zone better. The user can acquire a plurality of images. These images are displayed as thumbnail images in the thumbnail view 52.

Another section on the display screen 48 is the instruction box 54 that provides the user with detailed instructions at each step and makes the system easier to use. Additionally, the system has controls for specifying the patient details (name, age, etc.), calibration, adding/deleting probes and for the simulation of the ablation. The system also provides a pull down menu for switching rendering views and to toggle the display of the probe placements.

The cryoprobes particularly adapted for this computer guided placement are those manufactured by the present assignee, Endocare, Inc., Irvine, Calif. When Enocare cryoprobes are utilized there may be up to eight probes (generally only about 4–5) that are used depending on the dimensions of the treatment zone and dimensions of the prostate. The urethra, which passes through the prostate, is one of the anatomic structures that usually should not be frozen during this surgery. Accordingly, the urethra is protected and kept warm with the urethral warming catheter. The bladder neck sphincter and the external sphincter are also structures that should be protected from freezing, and these are protected from freezing by the warming catheter. A transrectal probe 18 is inserted into the rectum in order to visualize the placement of the probes and the growth of the iceballs formed by the cryoprobes. (As noted above, alternative imaging means may be utilized.) To assist in placement of the cryosurgical probes, a template 21 is used which supports the probes 22 during insertion and while they are installed in the body. The patient is placed in the lithotomy position, i.e. horizontally on an operating table with legs positioned to provide access for the ultrasound probe 18 to be inserted into the rectum and cryoprobes 22 to be inserted through the perineal area into the prostate.

The transrectal ultrasound probe 18 is used to visualize the prostate and the cryosurgical probes. A stepper assembly 16 provides the required advance. The ultrasound probe operates in the range of about 2–10 MHz, depending on the equipment used (the process described herein may be used with any ultrasound probe and ultrasound generator, which may be selected based on various technical, medical and budgetary considerations). As mentioned, the image is displayed as a two dimensional representation of the boundaries of the prostate.

The image shown is refreshed at a regular rate by the ultrasound imaging system and the images may shift with movement of the ultrasound probe. The surgeon is instructed to translate the ultrasound probe within the rectum to obtain several cross sectional views and to choose the largest viewable cross section of the prostate for analysis and display.

The system provides a function for the operator to freeze the image in order to accept outlining and path-finding inputs followed by calculating functions. The operator is prompted to orient the ultrasound image such that the rectal wall is substantially parallel to the bottom edge of the display area. The operator is instructed to acquire a series of images. In response to the operator's instruction to the system to capture an image, a single frame will be grabbed by the system software and displayed as an image. The captured images are presented on the display to allow the operator to interact with the system to determine the size and shape of the prostate.

The system provides the operator with a suitable interface for outlining the prostate treatment zone and other anatomical structures of interest such as the urethra or rectal wall. The detailed description of U.S. Pat. No. 6,139,544 goes into substantial detail as to the operator system interactions for providing outlining. U.S. Pat. No. 6,139,544 is incorporated herein by reference.

The computer system searches the display data for the outline and defines the two parameters H2 and L2. The parameter H2 is the "height" of the prostate that will be considered by the system. The parameter L2 is the length of the prostate that will be considered by the program. (It should be appreciated that any variable name may be assigned to these parameters; the H2 and L2 designations correspond to variables used in the computer program which the present inventors have devised to implement the system.) At this point, the computer system analyzes the variables to assist the operator in deciding how to accomplish the cryosurgery. If L2 is greater than 35 mm, the system will notify the operator that a pullback freeze is required to completely ablate the prostate. The doctor will then be apprised that a single freezing operation will be insufficient, and that the cryosurgery must be accomplished in two steps, with a first freeze being accomplished with the probe tips near the top of the prostate and the second freeze be accomplished afterward, with the cryoprobes pulled back about 10 mm toward the apex of the prostate. If H2 is less than a predetermined distance from either end of the prostate, the system will prompt the operator to verify that the outline accurately reflects the size and shape of the prostate, whereupon the process may continue or be restarted.

The number of cryoprobes needed is determined. This involves computing the area of the treatment zone in the largest image. The length along the outline of the treatment zone is computed. The length of the treatment zone periphery is used to compute the number (N) of probes and the distance b between the probes. Once the number of probes, N, is computed the first probe is placed at approximately a distance 'a' from the anterior tip of the prostate. The distance a is approximately half of the distance b between the probes.

After computing the location of the first probe the location of the second probe is computed by choosing a location at approximately a distance b from the first probe along the length of the treatment zone periphery. A horizontal line is determined that passes through the location of the first probe and intersects the prostate periphery. This position is moved along the horizontal line until the distance between the probe and the prostate periphery is approximately a. This specifies the position of the second probe. The positions of the remaining N-2 probes are similarly computed. The last probe is positioned so that it is below the urethra a sufficient height from the posterior tip of the prostate and a marginal distance laterally from the center of the urethra so that the probe does not get too close to the urethra. After calculation of the optimal placement of the cryoprobes according to the method above, the system graphically displays the desired locations to assist the operator in placing the actual probes in the prostate of the patient. The optimal location of the probes is indicated in the horizontal cross section by a graphic representation overlaid over the live ultrasound images and/or still images. FIG. 4 is an illustration of the system output indicating the optimum placement of cryoprobes within the prostate horizontal cross sectional image shown in FIG. 3. The suggested probe placement is indicated by graphical markers 60, 62, 64, 66 for Probes 1, 2, 3 and 4, respectively. The markers are placed in the display by the computer system, overlaying the ultrasound image of the prostate horizontal cross section.

Figure 5:
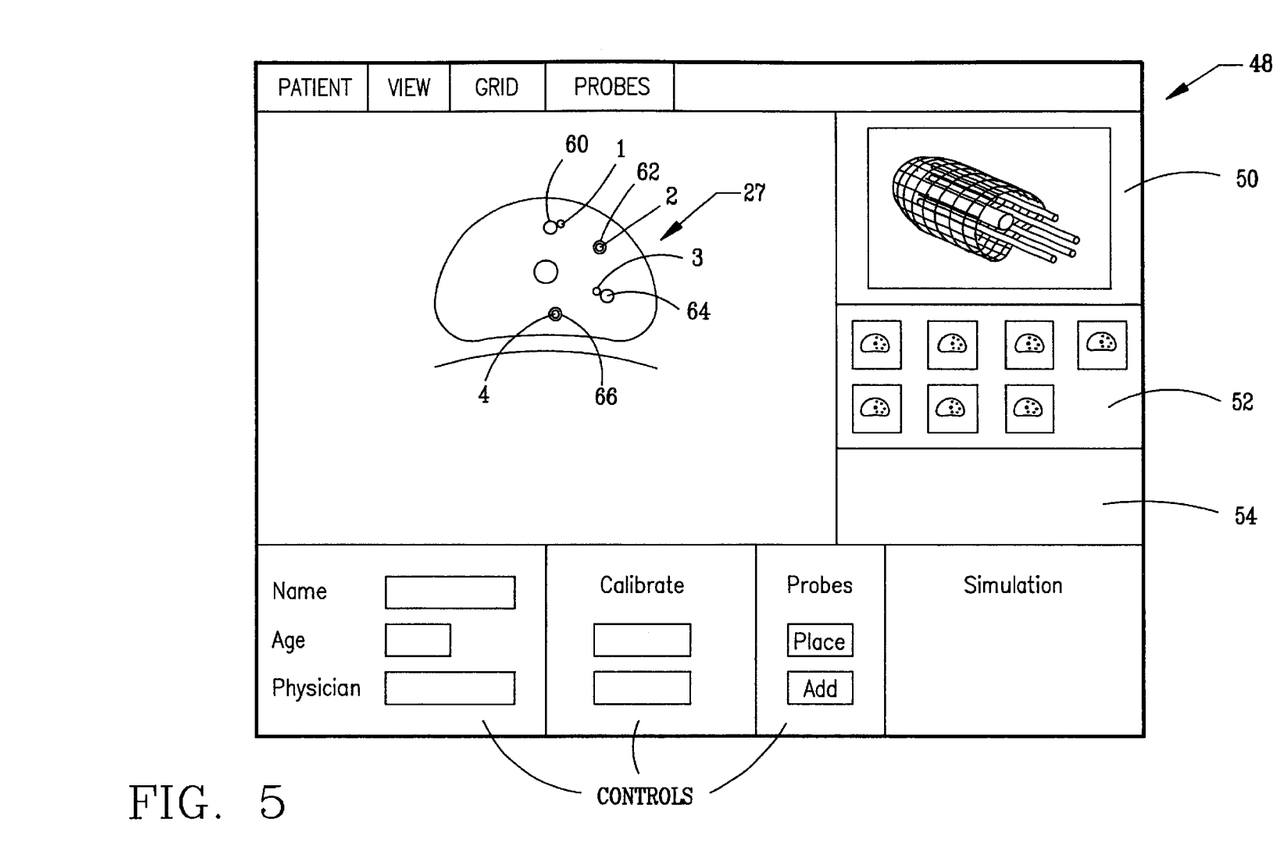
FIG. 5 is another example of the computer display, illustrating the system output showing the actual placement of cryoprobes in relation to the displayed optimum placement of cryoprobes with the prostate image shown in FIG. 4.

With the optimal probe placements calculated and graphical markers placed on the display, the operator may insert cryoprobes into the prostate. FIG. 5 illustrates the feedback provided to the operator indicating the actual position of the cryoprobes in relation to the suggested placement shown in FIG. 4. The graphical markers 60, 62, 64 and 66 are shown in the horizontal cross section, displayed as generated by the computer system. In addition, the ultrasound image of the probes is displayed in the display area (designated respectively as 1, 2, 3 and 4), since the probes enter the ultrasound imaging field and are imaged by the ultrasound imaging system. As the surgeon inserts each probe into the prostate, its placement as indicated by the ultrasound system may be compared to the suggested probe placement, and the surgeon may manipulate the probes so that the ultrasound images of the actual probes align with the graphical markers. Probe 1 has been placed in a position different than its associated graphical marker 60, and the surgeon may decide on that basis to reinsert the probe to more closely align it with the marker. Probe 2 has been placed in good correspondence with the template provided by the computer, and the ultrasound image is aligned with the graphical marker 62. Probe 3 has been placed close to the marker 64, and the surgeon may decide to reposition the probe or to leave it in place. Likewise, Probe 4 appears in the display on or near its associated marker 66, providing feedback to the surgeon ensuring proper placement of the probes.

Figure 6:
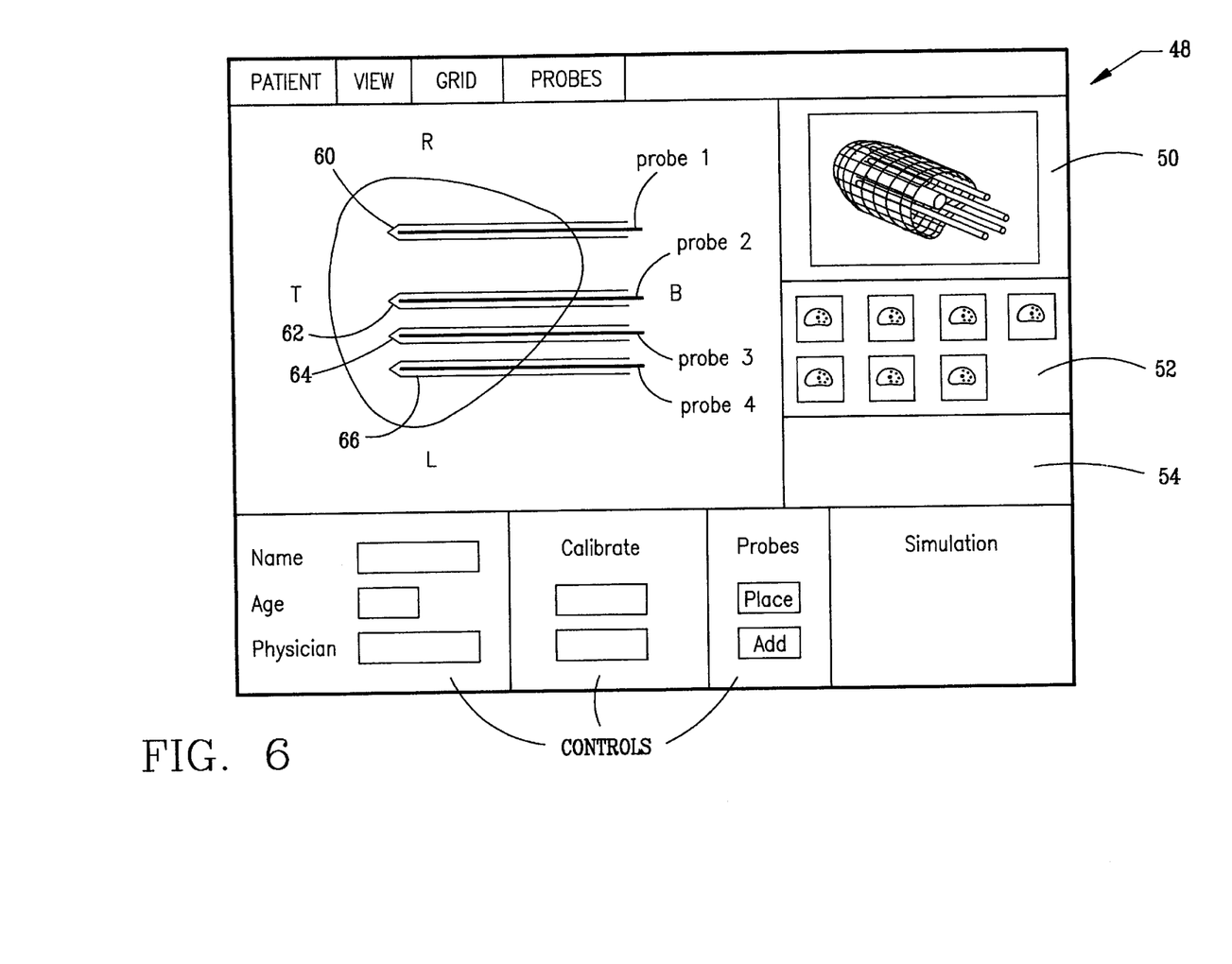
FIG. 6 is another example of the computer display, showing another view of the cryoprobes with the prostate image.

Referring to FIG. 6, another display is shown, again illustrating the graphical markers 60, 62, 64 and 66. The ultrasound images of the probes are also displayed in the display area. Again, the surgeon may view the ultrasound image of the actual probes, and place the probes as closely as possible positions corresponding to the markers. These displays help the operator in placing the probes as desired in parallel relationship with the ultrasound probe and the rectal wall. The operator may switch repeatedly between the displays of FIGS. 5 and 6 while inserting the cryoprobes, selectively displaying the image of the horizontal cross section and the image of the coronal cross section, to monitor the progress of the probes and ensure placement of the probes is accomplished in the positions suggested by the computer system. When cryoprobe placement is satisfactory, the surgeon will start the flow of cooling gas to freeze the prostate. The freezing operation can be confirmed in the ultrasound image by watching the iceballs (the mass of frozen tissue) around each cryoprobe form. The extent of the iceballs and the extent of the prostate that is frozen is monitored to ensure that substantially all of the desired treatment zone of the prostate is frozen. The freezing process may be repeated to ensure the desired ablation of the prostate. There may be instances where the treatment zone includes two or more treatment sections. This might occur if more than one small foci of low grade disease are found within the prostate.

The computer program that performs the desired calculations may be in any suitable program language such as C++ or Java. Alternatively, an embedded system could be programmed.

Thus, we have described a system for assisting surgeons in performing cryosurgery of the prostate by calculating optimal positions for cryoprobes and providing display based templates for overlay over an ultrasound image display, and displaying actual cryoprobe ultrasound images together with template images so that the surgeon may compare suggested and actual placement of the probes, and adjust placement accordingly. The method and system is described above in relation to our CRYOCARE™ cryosurgical system, which is provided with up to eight independently controlled 3 mm argon powered cryoprobes. The system cools the probes to cryosurgically effective temperatures (typically below −120° C.) through Joule-Thomson cooling within the probe tips. If used for cryogenic ablation the system may be implemented with other cooling systems such as liquid nitrogen cryoprobes and mixed gas cryoprobes. The placement of probes is calculated based on this system, and the calculations may be adjusted for different systems and numbers of probes. The system may be adapted to other forms of ablation and treatment of the prostate, with adjustments in the calculations being made to account for the ablative range of the devices. Other ablative elements may include, for example, radio frequency devices, microwave devices, high intensity focused ultrasound devices, lasers, radioactive seeds and ablation agents such as chemicals, e.g. alcohol-based substances. Thus, while the preferred embodiments of the devices and methods have been described in reference to the environment in which they were developed, they are merely illustrative of the principles of the invention. Other embodiments and configurations may be devised without departing from the spirit of the invention and the scope of the appended claims.

What is claimed is:

1. A computer system for the focal treatment of prostate cancer, said computer system being capable of acquiring and displaying images of the prostate of a patient for assisting a surgeon in placing ablative elements in the prostate of the patient, said computer system being programmed with software capable of performing the following steps:

determining the dimensions of the prostate;

determining the dimensions and location of a treatment zone, said treatment zone being determined to include only one neurovascular bundle of the prostate and exclude the other neurovascular bundle of the prostate; and, utilizing said determined dimensions of the prostate and treatment zone for computing the number and location of ablative elements needed to treat the treatment zone while minimizing any adverse effect on the patient's sexual function.

2. The computer system of claim 1, wherein said step of utilizing said determined dimensions of the prostate and treatment zone comprises the steps of:

computing the number (N) of ablative elements;

computing a distance (b) between the ablative elements so that the ablative elements are placed approximately equidistant from each other in said treatment zone;

computing a first position for placement of a first ablative element;

computing a second position for placement of a second ablative element, the second position being at said distance, b, from said first position and a distance a from the prostate periphery, wherein a is approximately ½ b; and, computing N-2 remaining positions for the ablative elements in substantially the same manner as said second position was computed.

3. The computer system of claim 2, wherein said step of computing said first position comprises computing a first position based on the dimensions of the treatment zone and location of the treatment zone within the prostate.

4. The computer system of claim 2, wherein said step of computing said first position comprises computing a first position based on the location of the center of the urethra.

5. The computer system of claim 2, wherein said step of computing said N-2 remaining positions for the ablative elements comprises computing N-2 ablative elements about the prostate periphery.

6. The computer system of claim 1, wherein said step of computing the number and location of ablative elements comprises computing the number and location of a set of cryoprobes.

7. The computer system of claim 1, wherein said step of computing the number and location of ablative elements comprises computing the number and location of a set of radioactive seeds.

8. The computer system of claim 1, wherein said step of computing the number and location of ablative elements comprises computing the number and location of a set of radio frequency devices.

9. The computer system of claim 1, wherein said step of computing the number and location of ablative elements comprises computing the number and location of a set of microwave devices.

10. The computer system of claim 1, wherein said step of computing the number and location of ablative elements comprises computing the number and location of a set of laser devices.

11. The computer system of claim 1, wherein said step of computing the number and location of ablative elements comprises computing the number and location of a set of high intensity focused ultrasound devices.

12. The computer system of claim 1, wherein said treatment zone comprises a plurality of treatment sections.

13. The computer system of claim 1, wherein said step of utilizing said determined dimensions of the prostate and treatment zone comprises the steps of:

computing a distance (b) between the ablative elements so that the ablative elements are placed approximately equidistant from each other in said treatment zone;

computing a first position for placement of a first ablative element based on the location of the center of the urethra;

computing a second position for placement of a second ablative element, the second position being at said distance, b, from said first position and a distance a from the prostate periphery, wherein a is approximately ½ b; and, computing N-2 remaining positions about the prostate periphery in substantially the same manner as said second position was computed, where N is the number of ablative elements.

14. A computer system for the focal treatment of prostate cancer, said computer system including a display for assisting a surgeon in placing cryoprobes in the prostate of a human patient, wherein the cryoprobes are inserted through the skin of the perineal area of the patient and into the prostate, the display being adapted to display images of the prostate, said computer system being programmed with software capable of performing the following steps:

determining the width of the prostate;

determining the height of the prostate;

determining the location of the center of the urethra;

determining a side of the prostate that is required to be treated, said side being defined as the treatment zone, said treatment zone being determined to include only one neurovascular bundle of the prostate and exclude the other neurovascular bundle of the prostate;

determining the number of cryoprobes (N) needed to freeze said treatment zone;

computing an distance (b) between the cryoprobes so that the cryoprobes are placed approximately equidistant from each other in said treatment zone;

computing an first position for placement of a first cryoprobe based on the location of the center of the urethra;

computing an second position for placement of a second cryoprobe, the second position being at said distance, b, from said first position and a distance a from the prostate boundary, wherein a is approximately ½ b; and, computing N-2 remaining positions in substantially the same manner as said second position was determined.

15. A system for the focal treatment of prostate cancer, comprising:

a) a computer guidance system including a display for assisting a surgeon in placing ablative elements in the prostate of a human patient, the display being adapted to display images of the prostate, said computer system being programmed with software capable of performing the following steps:

determining the dimensions of the prostate;

determining the dimensions and location of a treatment zone, said treatment zone being determined to include only one neurovascular bundle of the prostate and exclude the other neurovascular bundle of the prostate; and, utilizing said determined dimensions of the prostate and treatment zone for computing the number and location of ablative elements needed to treat the treatment zone while minimizing any adverse effect on the patient's sexual function;

b) an imaging system connectable to said computer guidance system for providing data for use by said computer guidance system; and, c) an ablative treatment system for providing the required prostatic ablation in response to an output provided by said computer guidance system.

\* \* \* \* \*